(12) United States Patent
Andersson et al.

(10) Patent No.: US 7,371,205 B2
(45) Date of Patent: May 13, 2008

(54) DEVICE FOR ASYMMETRIC HEATING AND COOLING OF REACTION MIXTURES DURING CENTRIFUGING AND ROTOR MEANS THEREFORE

(75) Inventors: Leif Andersson, Atvidaberg (SE); Mats Malmqvist, Uppsala (SE)

(73) Assignee: Alphahelix Molecular Diagnostics AB, Uppsala (SE)

( * ) Notice: Subject to any disclaimer, the term of this patent is extended or adjusted under 35 U.S.C. 154(b) by 0 days.

(21) Appl. No.: 10/535,137

(22) PCT Filed: Nov. 18, 2003

(86) PCT No.: PCT/SE03/01781

§ 371 (c)(1),
(2), (4) Date: Jan. 25, 2006

(87) PCT Pub. No.: WO2004/045774

PCT Pub. Date: Jun. 3, 2004

(65) Prior Publication Data

US 2006/0142134 A1    Jun. 29, 2006

(30) Foreign Application Priority Data

Nov. 19, 2002    (SE) .................................... 0203413

(51) Int. Cl.
*B04B 5/02* (2006.01)
*B04B 15/02* (2006.01)

(52) U.S. Cl. .......................................... 494/14; 494/16

(58) Field of Classification Search ............ 494/13–14, 494/16–21, 23, 25–26, 60; 210/175, 180; 422/72

See application file for complete search history.

(56) References Cited

U.S. PATENT DOCUMENTS

| 1,700,186 | A | * | 1/1929 | Squire et al. ................. 494/60 |
| 2,699,289 | A | * | 1/1955 | Allen et al. .................. 494/16 |
| 2,778,566 | A | * | 1/1957 | Garrett ........................ 494/13 |
| 2,878,992 | A | * | 3/1959 | Pickels et al. ............... 494/14 |
| 2,917,229 | A | * | 12/1959 | Di Benedetto et al. ....... 494/14 |
| 3,148,146 | A | * | 9/1964 | Asnes et al. ................... 494/1 |
| 3,600,900 | A | * | 8/1971 | Buddecke .................... 494/20 |
| 3,860,166 | A | * | 1/1975 | Anderson .................... 494/13 |
| 4,053,104 | A | * | 10/1977 | Penhasi et al. ............... 494/14 |
| 4,193,536 | A | * | 3/1980 | Kubota ........................ 494/14 |
| 4,221,325 | A | * | 9/1980 | Kubota ........................ 494/14 |

(Continued)

FOREIGN PATENT DOCUMENTS

DE    2611679    *    9/1977

(Continued)

*Primary Examiner*—Charles E. Cooley
(74) *Attorney, Agent, or Firm*—Dowell & Dowell, PC

(57) ABSTRACT

A rotor assembly for centrifuging reaction vessels containing reaction mixtures in a device for asymmetric heating and cooling of reaction mixtures during centrifugation. The rotor contains at least one fan blade used to force ambient gas to pass the reaction mixture. Also provided is a device for asymmetric heating and cooling of reaction mixtures during centrifugation.

13 Claims, 5 Drawing Sheets

U.S. PATENT DOCUMENTS

| | | | | |
|---|---|---|---|---|
| 5,490,830 | A * | 2/1996 | Lovelady et al. | 494/14 |
| 5,724,819 | A * | 3/1998 | Boeckel et al. | 62/3.7 |
| 5,772,572 | A * | 6/1998 | Koch et al. | 494/14 |
| 5,897,483 | A * | 4/1999 | Koch et al. | 494/14 |
| 6,068,586 | A * | 5/2000 | Koch et al. | 494/14 |
| 6,783,993 | B1 | 8/2004 | Malmquist | |
| 7,192,394 | B1 * | 3/2007 | Karl | 494/14 |
| 2005/0043163 | A1 * | 2/2005 | Malugvist et al. | 494/14 |
| 2006/0142134 | A1 * | 6/2006 | Andersson et al. | 494/14 |

FOREIGN PATENT DOCUMENTS

| | | | |
|---|---|---|---|
| DE | 10017318 A1 | * | 10/2001 |
| DE | 10316897 A1 | * | 11/2004 |
| DE | 102004058247 A1 | * | 6/2006 |
| EP | 0455876 A2 | * | 11/1991 |
| JP | 54-117975 | * | 9/1979 |
| JP | 61-13161 | * | 1/1986 |
| JP | 10-85627 | * | 4/1998 |
| JP | 2000-93847 | * | 4/2000 |
| JP | 2000-107642 | * | 4/2000 |
| JP | 2003-275621 | * | 9/2003 |
| JP | 2005-230749 | * | 9/2005 |
| SU | 1271577 A1 | * | 11/1986 |
| WO | WO 0058013 | | 10/2000 |
| WO | 03/000428 | * | 1/2003 |
| WO | 2004/045774 A1 | * | 6/2004 |

* cited by examiner

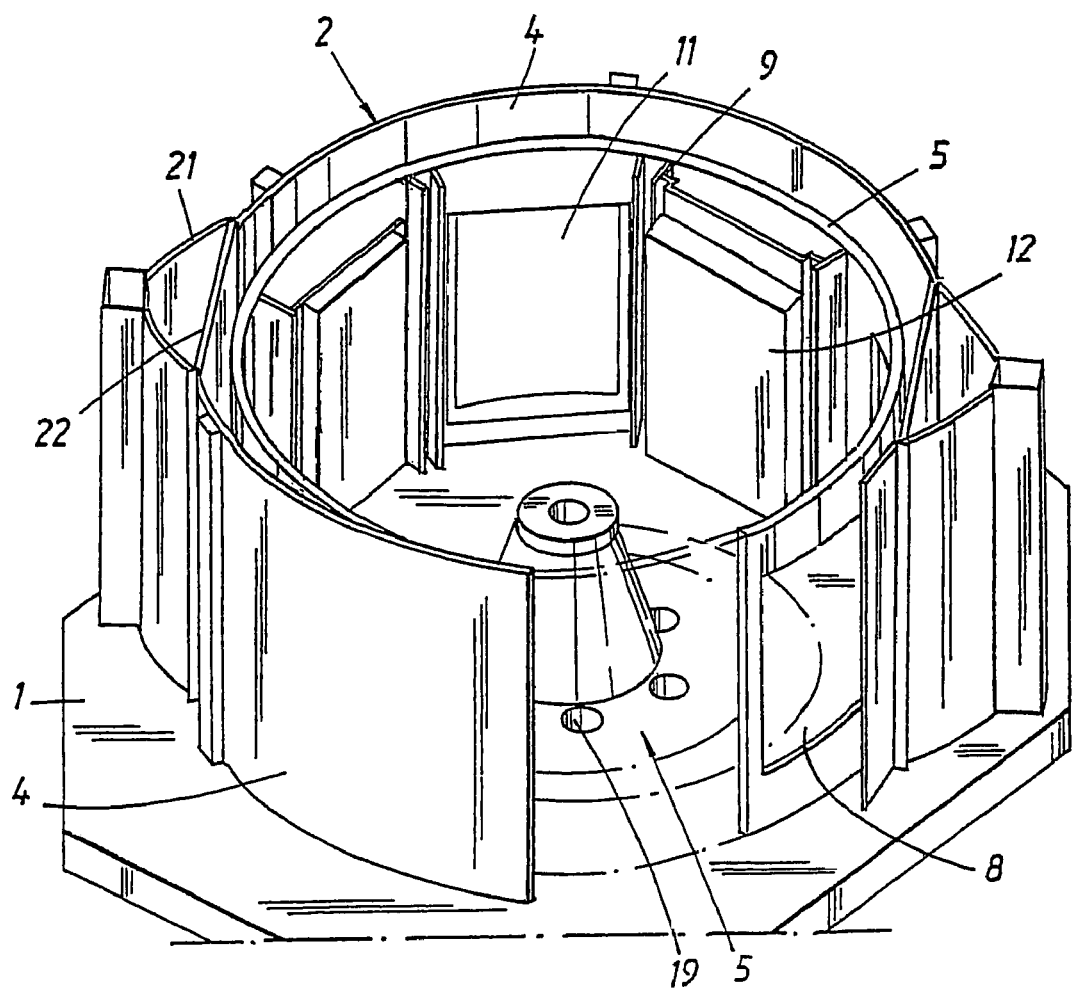

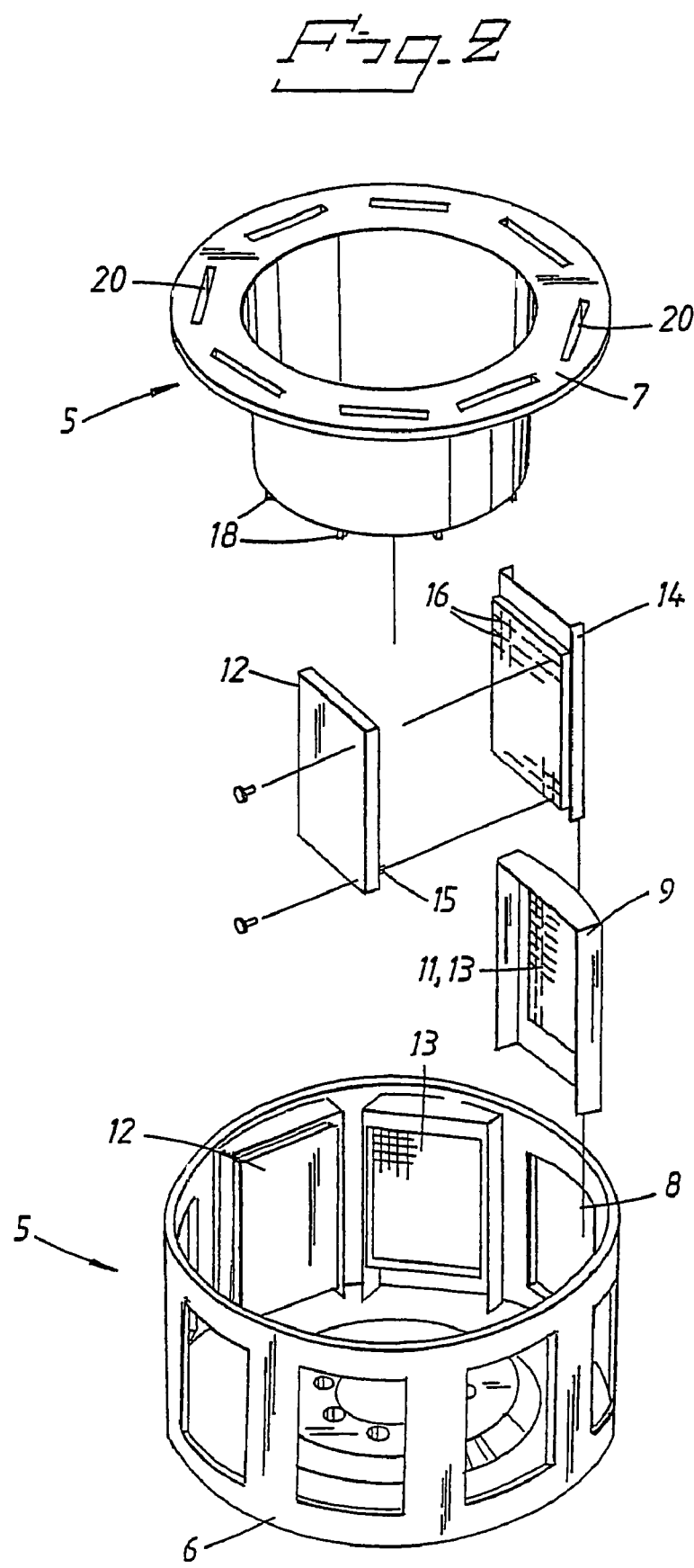

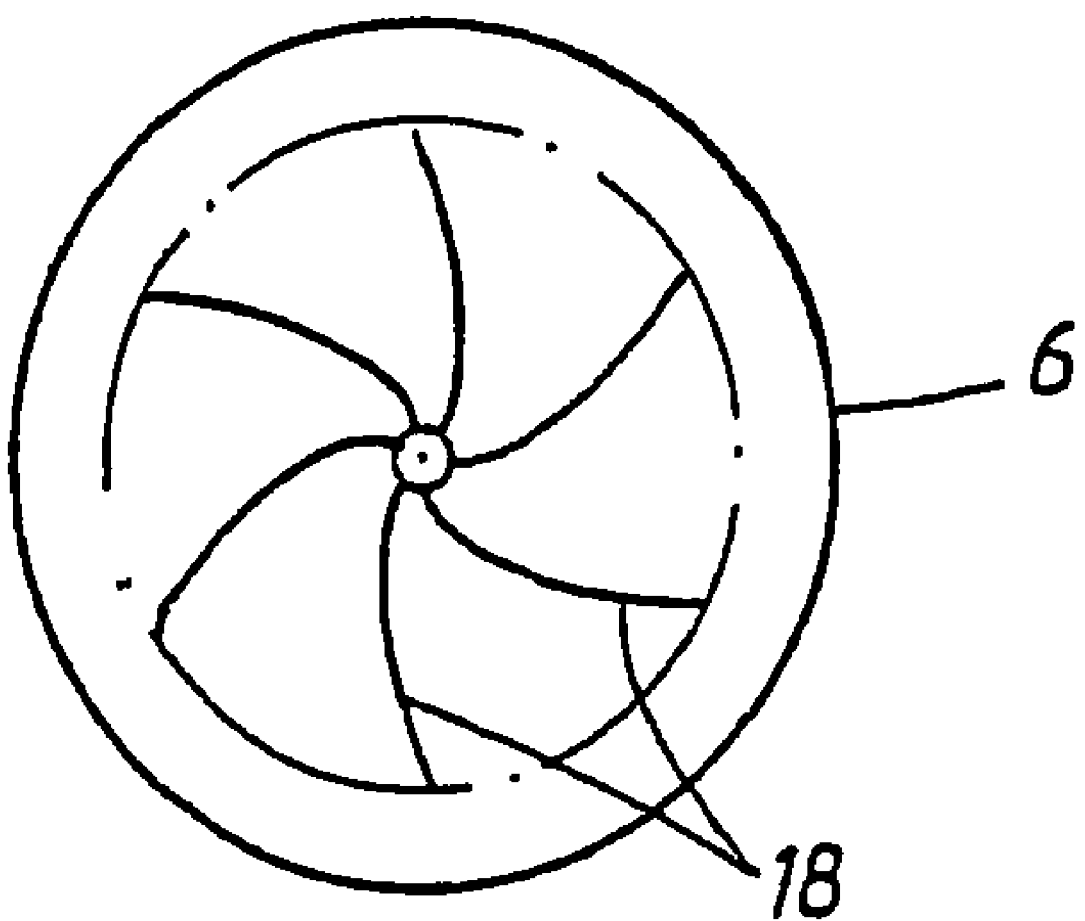

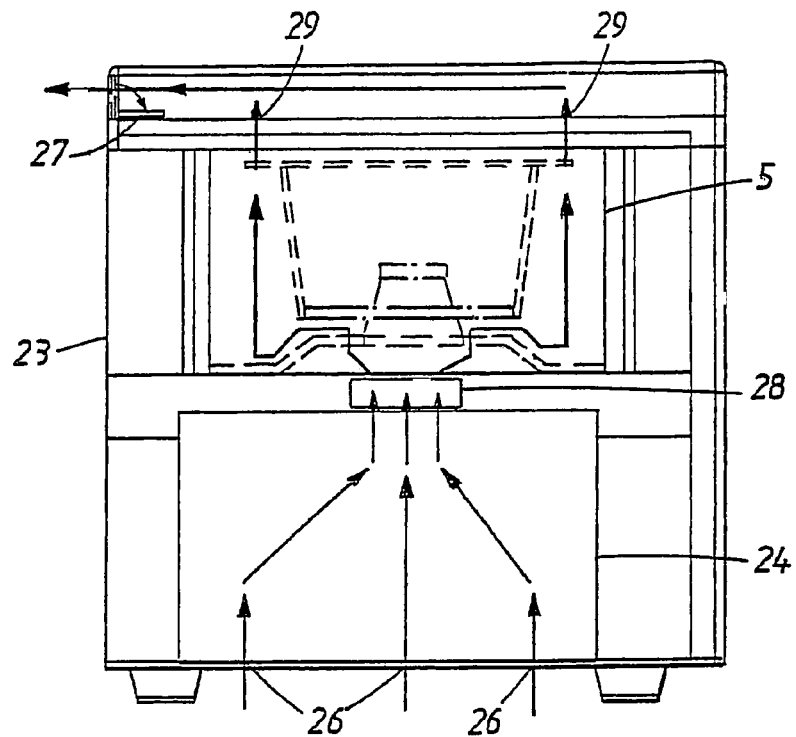
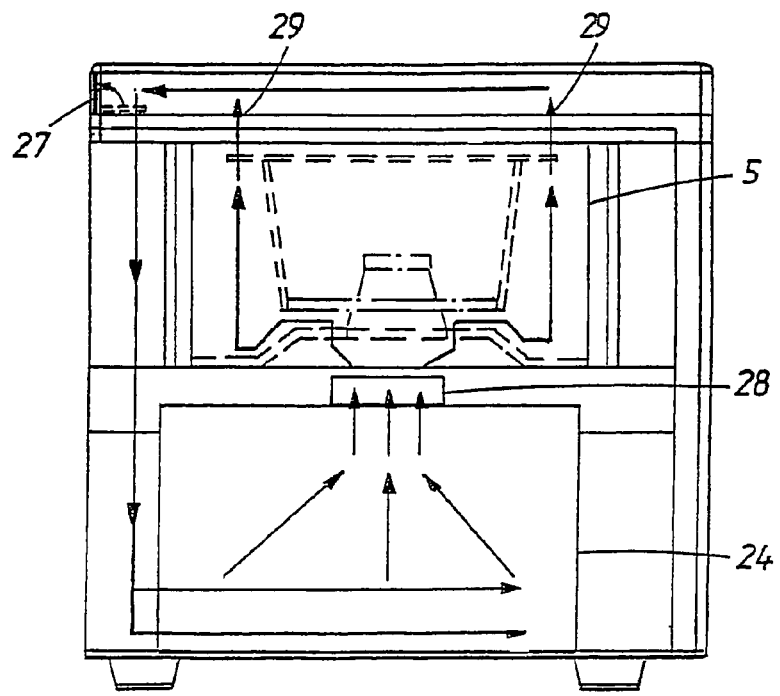

DEVICE FOR ASYMMETRIC HEATING AND COOLING OF REACTION MIXTURES DURING CENTRIFUGING AND ROTOR MEANS THEREFORE

CROSS REFERENCE TO RELATED APPLICATIONS

This application is a National Phase of PCT Application PCT/SE2003/001781 filed Nov. 18, 2003 in the name of Leif Andersson and Mats Malmqvist entitled, DEVICE AND ROTOR MEANS THEREFOR.

The present invention relates to rotor means for centrifuging reaction vessels containing reaction mixtures in a device for asymmetric heating and cooling of reaction mixtures during centrifugation and a device for asymmetric heating and cooling of reaction mixtures during centrifugation having such a rotor means.

TECHNICAL BACKGROUND

The applicant has developed a method and an apparatus for rapid homogenisation and mixing of reaction mixtures with regard to temperature and chemical concentration, i.e. to subject the reaction mixtures to asymmetric heating and cooling while the reaction mixtures are centrifuged.

When using said apparatus, reaction vessels including the reaction mixtures, i.e. the complete reaction mixture or a subset of this, are placed in a rotor of a centrifuge with the closed end directed downwards, outwards or otherwise according to standard practice for centrifuging the reaction vessels in question. The centrifuge is then started, i.e. the engine which brings the rotor to spin is switched on.

When the rotor has accelerated to the chosen gravitational force, the rotation is kept at constant speed. A heating source is now switched on leading to an increased temperature in the reaction mixtures in an asymmetric manner so that a temperature difference is created in the reaction mixtures. Preferably, the heating acts directly on a portion of the reaction mixtures contained in the reaction vessels. At the same time the reaction mixtures are subjected to cooling by means of cooling the walls of the reaction vessels.

This asymmetric heating and cooling during centrifugation creates a rapid, controlled flow in the reaction vessels that thoroughly mixes the reaction mixtures with respect to both temperature and chemical concentration. This extremely rapid mixing is tentatively called superconvection.

SUMMARY OF THE INVENTION

Accurate, fast and effective cooling of the reaction mixtures is important in order to decrease process time and the quality of the outcome, for example to minimize or counteract unwanted side reactions.

The solution to the problem of creating effective cooling is provided by novel rotor means having the features according to claim 1 and by a novel device for asymmetric heating and cooling of reaction mixtures during centrifugation having rotor means according to the present invention.

By the provision of at least one fan blade in the rotor means, ambient gas is forced to pass the reaction mixtures, whereby, for example, a more effective cooling of the reaction mixtures may be performed since a larger amount of ambient gas will pass the reaction mixtures than if the reaction mixtures would only be subjected to the ambient gas by the rotational speed of the rotor. The function of the fan blade/-s may be compared with the function of a centrifugal pump.

In order to effectively perform the cooling of the reaction mixtures, the ambient gas could, be conducted through a conducting passage.

According to a preferred embodiment the rotor means comprises a base portion and a lid portion, forming an inner space between these two portions. Within this inner space the fan blade/-s are provided.

Preferably the lower portion of the rotor means, for example but not necessarily the base portion, is provided with at least one through hole to let the gas into the inner space, or more precisely, the gas will be drawn into the inner space by the performance of the rotating fan blade/-s in the inner space. Preferably the upper portion of the rotor means, for example the lid portion but not necessarily, is provided with at least one through hole to let the gas, which is drawn in and forced through the inner space, out of the inner space.

The fan blade/-s may for example be arranged on the inside, i.e. the side that faces the inner space, of the lid portion or on the inside of the base portion.

In order to increase the throughput of the device and/or process, it would be an advantage to be able to handle more reaction mixtures at the same time. One way of doing this is to handle reaction mixtures arranged in a parallel format, for example in at least one microtitre plate. Microtitre plates are available in different formats, such as the traditional 96 well format, and e.g. the more dense 384 well format, as well as the 1536 well format.

Using microtitreplates, the benefits of the intention become accentuated. If only the airflow caused by the rotation velocity is used to cool the reaction vessels containing the reaction mixtures, a problem of non-uniform cooling of the reaction mixtures will appear. The airflow will hit the row of reaction vessels in the front, in relation to the direction of movement of the microtitre plate, whereafter, due to natural flow, the airflow will be diverted outside the closed ends of the reaction vessels of the microtitre plate towards the back of the plate.

Thanks to the present invention it becomes possible to evenly cool all the reaction mixtures in the microtitre plate by forcing ambient gas to pass in between the wells containing the reaction mixtures by means of at least one fan blade and at least one gas conducting passage provided in the rotor means.

The gas may be ambient air or any gas supplied to the rotor means and its surroundings. The air or gas may be cooled by cooling means.

Yet another problem that arises in particular when reaction vessels in the parallel format, e.g. microtitre plates, are used is that of deformation of the reaction vessels. Under the high centrifugal forces and elevated temperatures, the microtitreplates are frequently deformed. According to conventional techniques, this is avoided by the provision of supporting elements shaped as a negative print of the microtitreplate. In other words, the microtitreplate is placed in a solid support having wells corresponding to each reaction vessel or well of the known art, the reaction vessels or wells are not accessible for analysis, nor for effective heating and cooling.

This problem is solved by means of the arrangement according to the present invention provides a highly beneficial solution to the problem of microtitreplate deformation. The base portion of the rotor which together with the lid portion define an inner space through which ambient air is forced, does simultaneously constitute a support for the microtitreplates without obstructing the airflow and thus allowing for efficient cooling. By providing a transparent base plate, the reaction vessels are available for analysis if desired. Optionally, the base plate may be provided with indentations corresponding to the apices of the reaction vessels.

It should be noted that the function of the rotor means according to the present invention may be advantageous not only during cooling but also during keeping s constant temperature in the reaction mixtures, e.g. incubation.

SHORT DESCRIPTION OF THE DRAWINGS

The present invention will be described by way of exemplifying embodiments in connection with the appended drawings.

FIG. 1 illustrates in a perspective view an inner portion of a device for centrifuging reaction mixtures according to a preferred embodiment of the present invention.

FIG. 2 illustrates in an exploded diagram rotor means according to a preferred embodiment of the present invention.

FIG. 3 illustrates in a view from underneath a portion of the rotor means having fan blades.

FIG. 6 illustrates it a cross section view a device according to a preferred embodiment of the present invention provided with cooling means. It also illustrates the flow of the gas during cooling.

FIG. 7 illustrates the device in FIG. 7 and the flow of the gas during a constant temperature phase.

DETAILED DESCRIPTION OF PREFERRED EMBODIMENTS

Figure 4:
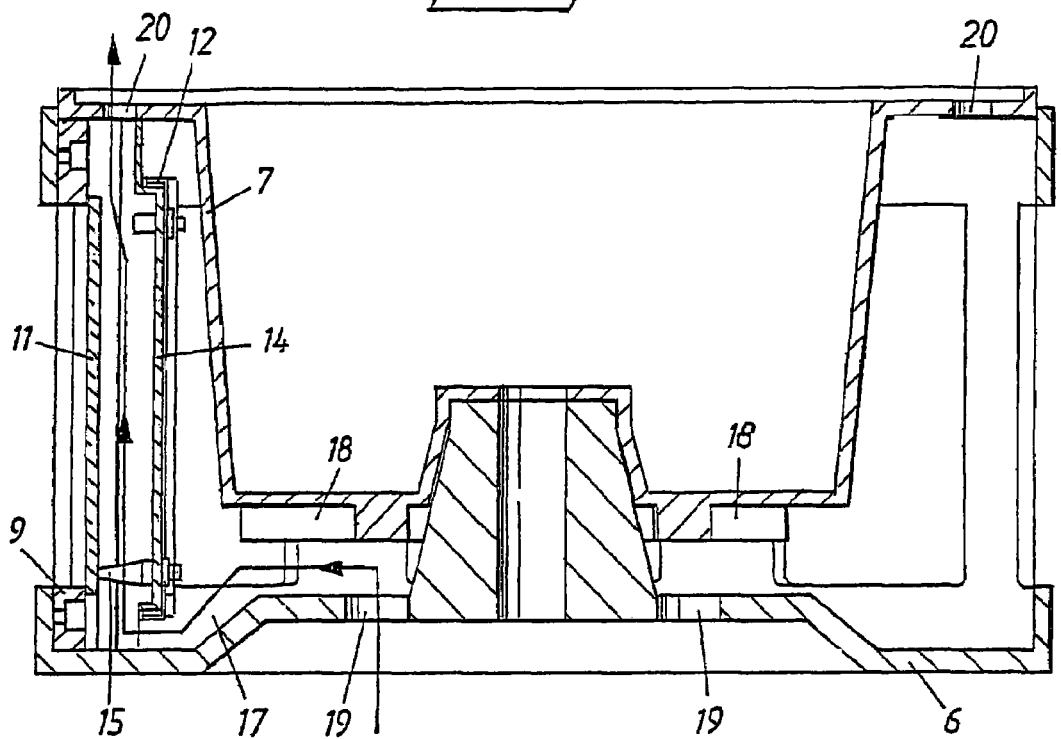
FIG. 4 illustrates in a cross section view the rotor means of the present invention.

FIG. 1 illustrates an inner portion of a preferred embodiment of a device for asymmetric heating and cooling of reaction mixtures- during centrifugation provided with rotor means according to the present invention. It comprises a bottom plate 1 and a substantially cylindrical wall 2 made up by wall portions 4.

Within the cylindrical wall 2 rotor means 5 (only centre by means of some kind of bearing and is for example connected to rotating means (not shown), such as a motor, preferably provided underneath the bottom plate 1.

In FIG. 2 the rotor means 5 and parts to be placed therein are shown in, an exploded view. The rotor means 5 comprises a base portion 6 and a lid portion 7. The base portion 6 is provided with side recesses 8 and in connection with each side recess 8 a guide portion 9 is mounted.

The guide portion 9 is also provided with a side recess 10, which is covered by a plate 11 of glass or another heat transferable material.

The above mentioned microtitre plate 12, comprising reaction mixtures, is mounted in a cassette 14, preferably with the wells 15 of the microtitre plates 12 protruding through adapted holes 16 in the cassette 14. The cassettes 14 may be adapted for different kinds of microtitre plates 12 or different cassettes 14 may be provided for different kinds of microtitre plates 12 but all the cassettes 14 are adapted to fit into the guide portions 9. The closed ends of the wells 15 of the microtitre plates 12 may rest against the plate 11 in the guide portion 9, at least during centrifuging.

The lid portion 7 is mounted on top of the base portion 6. Thus, an inner space 17 is formed between the base portion 6 with its mounted guide portions 9 and the lid portion 7, see FIG. 4. In the preferred embodiment fan blades 18 are arranged at the bottom of the lid portion 7 at the side which faces the inner space 17.

Figure 5:
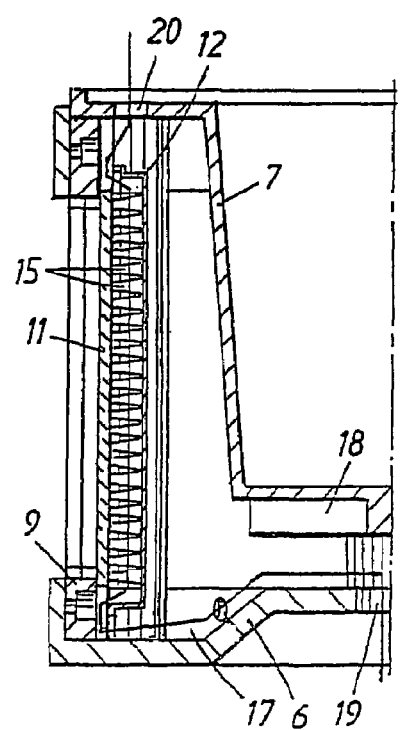
FIG. 5 illustrates a close up view of the rotor of FIG. 5 with a microtitre plate mounted.

The fan blades 18 will have the same kind of function as a centrifugal pump when the rotor means 5, and thereby the fan blades 18, rotate. The fan blades 18 are preferably arranged so that when they rotate they draw ambient gas into the inner space 17 through holes 19 arranged in the base portion 6, see arrows in FIG. 5, and force the ambient gas through the inner space 17 and out of holes 20 in the lid portion 7.

The holes 16 in the lower portion of the rotor means 5 are preferably arranged close to the rotational centre and the holes 20 in the upper portion of the rotor means 5 are preferably arranged along the cassettes 14, on the outsides thereof.

Since the only way out for the forced flow of gas is through the holes 20 and the fact that the cassettes 14 are in close contact with the lid portion 7 the gas will be forced underneath the cassettes 14 and in between the wells 15 of the microtitre plates 12, which wells 15 are positioned between the plates 11 covering the side recesses 10 of the base portion 6 and the cassettes 14, and up and out of the holes 20. This is shown by arrows both in FIG. 5 and FIG. 6. In other words, a conducting passage is provided to conduct the forced flow of gas to pass the reaction mixtures.

It is conceivable to provide baffles (not shown) in front of the lowest row of wells 15 of the microtitre plate 12 to disturb the forced gas flow so that this row will not directly be hit by the gas flow, which is forced to pass underneath the cassette 14.

If the microtitre plates 12 are provided with upper and lower side edges that could obstruct the gas flow between the wells 15 thereof, these upper and lower side edges will be fully or partially removed. The direction is related to the position when mounted in the rotor means 5.

Outside of the substantially cylindrical wall 2 a burst wall is provided for safety reasons, and having insulation provided there between. In FIG. 7 an embodiment of the device according to the present invention is illustrated, which is provided with cooling means 24. The burst wall, cylindrical wall 2 and the rotor means 5 are provided in the upper portion of a box like housing 23, which comprises an openable lid 25. The lid 25 is preferably sealed along its outer rim. For example the cooling means 24 may be a compressor cooling arrangement.

Gas canals and valves are provided in the housing 23, see the arrows showing the flow through the housing 23 during a cooling phase in the process in FIG. 7. In the bottom of the cooling means 24 at least one inlet valve 26 is provided that in open position take in ambient air to be cooled by the cooling means 24. In the lid 25 at least one outlet valve 27 and at least one transfer valve 29 is provided. The transfer valve 29 leads into an outlet canal in the lid, which leads to the outlet valve 27.

When the outlet valve is open the cooling gas, in this embodiment ambient air, may leave the housing 23 and at the same time a recycling canal is closed by the outlet valve 27. During a constant temperature phase of the process, see FIG. 8, the outlet valve 27 is closed and the gas cannot leave the housing 23 but instead the recycling canal is open so that the gas can be recycled into the cooling means 24. The inlet valve 26 is then closed.

Between the cooling means 24 and the rotor means 5 a centre valve 28 is provided. During the two above mentioned process phases the centre valve 28 is open to let gas into the rotor means 5 from the cooling means 24.

The invention claimed is:

1. A centrifuging reaction vessel assembly for asymmetric heating and cooling of the reaction mixtures during centrifugation, comprising a rotor means for mixing reaction mixtures, said rotor means supporting at least one microtitre plate for centrifuging reaction mixtures, said rotor means including at least one fan blade for directing ambient gas into an inner space formed between a base portion and a lid portion of said rotor means which enables gas flow to pass in direct contact with said at least one microtitre plate disposed in said inner space.

2. The assembly of claim 1, further comprising at least one gas conducting passage which is arranged in said base portion of said rotor means for allowing the ambient gas to pass the reaction mixtures.

3. The assembly of claim 2, wherein said at least one gas conducting passage is arranged to conduct the ambient gas between reaction mixture-containing wells of said at least one microtitre plate.

4. The assembly of claim 1, wherein said base portion and said lid portion define said inner space there between and in which said at least one fan blade is arranged.

5. The assembly of claim 4, wherein said at least one fan blade is arranged at an inside of said base portion of said rotor means.

6. The assembly of claim 4, wherein said at least one fan blade is arranged at a bottom of said lid portion at a side which faces said inner space formed between said base portion and said lid portion of said rotor means.

7. The assembly of claim 1, wherein a lower region of said rotor means is provided with at least one through hole throughwhich the ambient gas can be drawn.

8. The assembly of claim 1 wherein an upper region of said rotor means is provided with at least one through hole throughwhich the ambient gas is let out.

9. The assembly of claim 1 further comprising a plate arranged to support said at least one microtitre plate.

10. The assembly of claim 9 wherein said plate has indentations corresponding to apices of reaction mixture-containing wells of said microtitre plate.

11. The assembly of claim 1, wherein the ambient gas is ambient air.

12. The assembly of claim 1, further comprising a cooling means for cooling the ambient gas being directed into said rotor means by said at least one fan blade.

13. A centrifuging reaction vessel assembly for asymmetric heating and cooling of the reaction mixtures during centrifugation, comprising: a rotor means for mixing reaction mixtures and said rotor means supporting a plurality of microtitre plates for centrifuging reaction mixtures, said rotor means including at least one fan blade for directing ambient gas into an inner space formed between a base portion and a lid portion of said rotor means which enables gas flow to pass in direct contact with said plurality of microtitre plates disposed in said inner space.

* * * * *